(12) United States Patent
Thesman

(10) Patent No.: US 11,429,930 B2
(45) Date of Patent: *Aug. 30, 2022

(54) METHODS FOR OPTIMIZING MANAGED HEALTHCARE ADMINISTRATION AND ACHIEVING OBJECTIVE QUALITY STANDARDS

(71) Applicant: Quality Standards, LLC, Wilmington, DE (US)

(72) Inventor: Debra Thesman, Marina Del Rey, CA (US)

(73) Assignee: QUALITY STANDARDS, LLC, Wilmington, DE (US)

( * ) Notice: Subject to any disclaimer, the term of this patent is extended or adjusted under 35 U.S.C. 154(b) by 138 days.

This patent is subject to a terminal disclaimer.

(21) Appl. No.: 16/730,614

(22) Filed: Dec. 30, 2019

(65) Prior Publication Data

US 2020/0135312 A1 Apr. 30, 2020

Related U.S. Application Data

(60) Continuation of application No. 15/239,454, filed on Aug. 17, 2016, now Pat. No. 10,606,983, which is a
(Continued)

(51) Int. Cl.
*G06Q 10/10* (2012.01)
*G16H 40/20* (2018.01)
(Continued)

(52) U.S. Cl.
CPC ........... *G06Q 10/10* (2013.01); *G06F 3/0482* (2013.01); *G06F 3/04842* (2013.01);
(Continued)

(58) Field of Classification Search
CPC ........ G06Q 10/10; G16H 20/40; G16H 40/20; G16H 10/60; G16H 15/00; G06F 3/0482; G06F 3/04842
(Continued)

(56) References Cited

U.S. PATENT DOCUMENTS

| 6,915,254 | B1 * | 7/2005 | Heinze | .................. G06F 40/20 704/9 |
| 2008/0004505 | A1 * | 1/2008 | Kapit | .................. G16H 10/60 600/300 |

(Continued)

OTHER PUBLICATIONS

Richard Farkas and Gyorgy Szarvas, "Automatic construction of rule-based ICD-9-CM coding systems"; BMC Bioinformatics 2008, 9(Suppl 3):S10 Published: Apr. 11, 2008 (Year: 2008).*

*Primary Examiner* — Joshua B Blanchette
(74) *Attorney, Agent, or Firm* — Stetina Brunda Garred & Brucker

(57) ABSTRACT

Healthcare is administered to members/enrollees of a healthcare plan according to objective quality standards. A patient population of eligible members/enrollees is identified and for each member/enrollee, medical information is aggregated via a web-based compilation of medical data from multiple sources that is continuously updated so as to provide an accurate, up-to-date and readily accessible compilation of a member/enrollee past diagnoses, healthcare history, medical procedures, medications and the like. Such member/enrollees are continuously tracked, on an individual basis, and monitored to ensure healthcare is delivered for a variety of specific medical conditions pursuant to objective health program quality criteria.

15 Claims, 13 Drawing Sheets

Related U.S. Application Data division of application No. 13/715,852, filed on Dec. 14, 2012, now abandoned, which is a continuation of application No. 13/712,776, filed on Dec. 12, 2012, now abandoned.

(51) Int. Cl.
| | | |
|---|---|---|
| *G16H 10/60* | (2018.01) | |
| *G16H 15/00* | (2018.01) | |
| *G06F 3/0482* | (2013.01) | |
| *G16H 20/40* | (2018.01) | |
| *G06F 3/04842* | (2022.01) | |

(52) U.S. Cl.
CPC ............ *G16H 10/60* (2018.01); *G16H 15/00* (2018.01); *G16H 20/40* (2018.01); *G16H 40/20* (2018.01)

(58) Field of Classification Search
USPC .......................................................... 705/2, 3
See application file for complete search history.

(56) References Cited

U.S. PATENT DOCUMENTS

| | | | | |
|---|---|---|---|---|
| 2008/0077443 A1* | 3/2008 | Singer | ................... | G16H 10/60 |
| | | | | 705/3 |
| 2010/0042435 A1* | 2/2010 | Kay | ....................... | G06Q 40/08 |
| | | | | 705/3 |
| 2012/0303378 A1* | 11/2012 | Lieberman | ............. | G06Q 10/10 |
| | | | | 705/2 |

* cited by examiner

RAF Report By Health Plan
Revenue 2013 vs. Revenue 2012

DOS 2012 - Basis for 2013 Revenue
DOS 2011 - Basis for 2012 Revenue

Revenue 2013 vs. Revenue 2012 ▼   [RAF by PCP]   [Export to Excel]   [Review Report]

For PCP: All providers

| HP Name | Current Enrollment | Revenue 2013 (DOS 2012) | | | % Change RAF Total | Avg Monthly Enrolled 2012 | Revenue 2012 (DOS 2012) | | |
|---|---|---|---|---|---|---|---|---|---|
| | | RAF Demo HHR | RAF HCC Claims | RAF Total | | | RAF Demo HHR | RAF HCC MOR & Claims | RAF Total |
| PACIFICARE | 376 | 0.445 | 0.547 | 0.993 | 15 | 373 | 0.443 | 0.416 | 0.861 |
| HEALTH NET | 722 | 0.423 | 0.672 | 1.095 | -17 | 716 | 0.479 | 0.848 | 1.327 |
| BLUE SHIELD | 24 | 0.310 | 0.609 | 0.919 | 18 | 14 | 0.318 | 0.457 | 0.775 |
| SCAN | 271 | 0.460 | 0.612 | 1.073 | 2 | 360 | 0.452 | 0.598 | 1.05 |
| BLUE CROSS | 9 | 0.423 | 0.680 | 1.104 | 7 | 8 | 0.424 | 0.604 | 1.028 |
| AETNA | 16 | 0.502 | 0.303 | 0.804 | 19 | 15 | 0.448 | 0.223 | 0.671 |
| EASY CHOICE HEALTH PLAN | 96 | 0.414 | 0.429 | 0.842 | 1 | 83 | 0.485 | 0.344 | 0.829 |
| TOTAL: | 1,604 | 0.436 | 0.610 | 1.046 | -6 | 1,569 | 0.462 | 0.651 | 1.113 |

FIG. 3

Demographics
Member ID:
DOB - Age/Sex:
Address:
Phone No:
Effective Date:
Health Plan:
Eligibility History

[Medical Record] [Add Diagnostic] [View Measure] [Add dates Diagnostic] [Make Call]

HEDIS Measures Due
Influenza vaccination

Health Status Indicator
PCP Visit: Y
Annual Assessment Visit: N
ESRD:
Hospice: Y
DOS 2012 Total RAF: 0
DOS 2011 Total RAF: 0
GFR:
GFR Stage:
OME & Supplies:

2012 Claims HCC (S):
(Limited to a. Click above for complete list)
55  Maj. Depressive, Bipolar, & Paranoid Disorders
74  Seizure Disorders and Convulsions
105 Chronic Obstructive Pulmonary Dis.

DOS 2012 ▼

| Summary | Member Data | Reviews | Member Info. | Comments | Utilization Mgmt |

Potential Health conditions

| | HCC | HCC Description | RAF | Review Category | Review Status | | Reviewed Date |
|---|---|---|---|---|---|---|---|
| ☐ | 21 | Protein - Calories Malnutrition | 0.700 | Chronic Condition | Open | [Review] | |
| ☐ | 131 | Renal Failure | 0.329 | Correct coding | Open | [Review] | 06/06/2012 |
| ☐ | 79 | Cardio - Respiratory Failure & Shock | 0.517 | Correct coding | Completed - No Diag | [Review] | 06/06/2012 |
| ☐ | 80 | Congestive Heart Failure | 0.367 | Correct coding | Completed - No Diag | [Review] | 01/06/2012 |
| ☐ | 55 | Maj. Depressive, Bipolar, & Paranoid Disorders | 0.316 | Chronic Condition | Auto Closed - Encounter Occured | [Review] | |
| ☐ | 55 | Maj. Depressive, Bipolar, & Paranoid Disorders | 0.316 | Chronic Review | Auto Closed - Encounter Occured | [Review] | |
| ☐ | 74 | Seizure Disorders and Convulsions | 0.239 | Chronic Review | Auto Closed - Encounter Occured | [Review] | |
| ☐ | 74 | Seizure Disorders and Convulsions | 0.239 | Chronic Condition | Auto Closed - Encounter Occured | [Review] | |
| ☐ | 100 | Chronic Obstructive Pulmonary Dis. | 0.357 | Chronic Condition | Auto Closed - Encounter Occured | [Review] | |

[Complete Review]

Diagnostic History

| Code | Description | HCC | 2012 | 2011 | 2010 |
|---|---|---|---|---|---|
| 1101 | Dermatophytopis of Nail | | - | - | Y |
| 2639 | Unspec Protein-calorie Malnutr | H | - | Y | - |
| 2769 | Electrolyte And Fluid Disorder | | - | - | NS |
| 2859 | Unspecified Anemia | | - | - | NS |
| 29620 | Maj. Dprsv O/o Single Epise Unspe | H | Y | Y | - |
| 29630 | Maj. Dprsv O/o Single Epise Unspe | H | Y | - | - |
| 3050 | Adj Disorder with Depressed Mo | | - | Y | - |
| 3331 | Essential other Spec Forms Tre | | Y | Y | - |
| 345 | Epilepsy And Recurrent Seizure | | - | Y | Y |
| 34500 | Gen Nonconvuls Epilepsy W/o Int | H | - | Y | Y |
| 34590 | Uns Epilepsy w/o Intract Epile | H | Y | Y | Y |

CPT History
Pathology Report
Surgery

| Code | Description | 2012 | 2011 | 2010 |
|---|---|---|---|---|
| 360 | Operating Room Services | - | - | Y |
| 3075F | Syst Bp Ge 130 - 139mm Hg | - | Y | - |
| 3076F | Diast Bp < 80 mm Hg | - | Y | - |
| 36415 | Routine Venipouncture | - | NS | - |
| 66584 | Cataract Surg w/o/, 1 Stage | - | - | Y |
| 66200 | Treat Eyelid by Injection | - | - | Y |

Radiology/ Imaging Studies
Radiology

| Code | Description | 2012 | 2011 | 2010 |
|---|---|---|---|---|
| 71022 | Chest X - ray | NS | - | - |

△ TOP

HCC Prevalence - Potential Improvement
All HCCs Summary

Group: SMG
PCP: All
County: Los Angeles
Active & Term members: 1,402
Average Enrollment: 1,283

| HCC | Description | No. of Members | Prevalence Rate | | | Potential Improvement | |
|---|---|---|---|---|---|---|---|
| | | | Group County | FFS County | Varianc | No. of Members | Annual Increase |
| 1 | HIV/AIDS | 2 | 0.16% | 0.38% | -0.22% | 2.9 | $13,924 |
| 2 | Septicemia/Shock | 15 | 1.17% | 1.68% | -0.51% | 6.9 | $53,085 |
| 5 | Opportunistic Infections | 6 | 0.47% | 0.28% | 0.19% | -2.4 | -$11,837 |
| 7 | Metastatic Cancer and Acute Leukemia | 15 | 1.17% | 1.87% | -0.70% | 9.0 | $206,789 |
| 8 | Lung, Upper GI Tract, and other Severe CAs | 11 | 0.86% | 1.87% | -1.01% | 13.0 | $126,242 |
| 9 | Lymph., Head/Neck, Brain, and Other Major CAs | 14 | 1.09% | 1.44% | -0.35% | 4.5 | $33,406 |
| 10 | Breast, Prostate, Colorectal & Other CAs & Tumors | 94 | 7.33% | 7.21% | 0.12% | -1.5 | -$2,957 |
| 15 | Diabetes w/ Renal or Periph, Circul, Manif. | 247 | 19.25% | 1.61% | 17.64% | -226.3 | -$887,871 |
| 16 | Diabetes w/ Neurol, or Other Spec'd Manif. | 47 | 3.66% | 1.71% | 1.95% | -25.1 | -$98,305 |
| 17 | Diabetes with Acute Complications | 0 | 0.00% | 0.50% | -0.50% | 6.4 | $25,164 |
| 18 | Diabetes w/ Ophthalm, or Unspec'd Manif. | 31 | 2.42% | 1.65% | 0.77% | -9.8 | -$38,562 |
| 19 | Diabetes without Complication | 124 | 9.66% | 11.04% | -1.38% | 17.6 | $23,691 |
| 21 | Protein-Calorie Malnutrition | 22 | 1.71% | 1.62% | 0.09% | -1.2 | -$9,574 |
| 25 | End-Stage Liver Disease | 7 | 0.55% | 0.25% | 0.30% | -3.8 | -$40,340 |
| 26 | Cirrhosis of Liver | 5 | 0.39% | 0.48% | -0.09% | 1.2 | $5,058 |
| 27 | Chronic Hepatitis | 7 | 0.55% | 0.43% | 0.12% | -1.5 | -$4,108 |
| 31 | Intestinal Obstruction/Perforation | 18 | 1.40% | 2.27% | -0.087% | 11.1 | $36,461 |
| 32 | Pancreatic Disease | 11 | 0.86% | 1.21% | -0.35% | 4.5 | $17,317 |

FIG. 7

Star and Pay for Performance Measures
Summary Report
For Measurement Year 2012

Measure Type: Star
Health Plan: All
PCP Name: All

[Refresh Data]

| Test Measure | Eligible Population | Compliant | Not Compliant | Needed To Meet 4 Stars | Needed To Meet 5 Stars | Rate | Benchmark | Star |
|---|---|---|---|---|---|---|---|---|
| Senior | | | | | | | | |
| Adult BMI Assessment | | | | | | | | |
| - BMI within measure year or prior year | 8392 | 7068 | 1324 | 0 | 0 | 84% | 73% | ***** |
| Breast Cancer Screening | | | | | | | | |
| - One or more mammograms | 2128 | 1529 | 599 | 43 | 170 | 72% | 80% | *** |
| Care for Older Adults | | | | | | | | |
| - Function Status Assessement | 1373 | 12 | 1361 | 838 | 1057 | 1% | 78% | * |
| - Medication Review | 1373 | 10 | 1363 | 906 | 1112 | 1% | 82% | * |
| - Pain Screening | 1373 | 18 | 1355 | 796 | 1181 | 1% | 87% | * |
| Cholesterol Management | | | | | | | | |
| - LDL-C-Screening | 1057 | 872 | 185 | 32 | 95 | 82% | 91% | *** |
| Colorectal Cancer Screening | | | | | | | | |
| - One or more Screenings | 9352 | 5946 | 3406 | 0 | 187 | 64% | 66% | **** |
| Comprehensive Diabetes Care | | | | | | | | |
| - Eye Exam | 3004 | 1142 | 1862 | 781 | 1051 | 38% | 73% | * |
| - HbA1c > 9% | 3004 | 2224 | 780 | 180 | 421 | 74% | 88% | *** |
| - LDL- C < 100 | 3004 | 1656 | 1348 | 0 | 330 | 55% | 66% | **** |
| - LDL-C Screening | 3004 | 2542 | 462 | 0 | 150 | 86% | 90% | **** |
| - Nephropathy | 3004 | 2738 | 266 | 0 | 0 | 91% | 89% | ***** |

FIG. 9

| Test Measure | Apr 12 Rate | May 12 Rate | Jun 12 Rate | Jul 12 Rate | Aug 12 Rate | Benchmark |
|---|---|---|---|---|---|---|
| Commercial | | | | | | |
| Senior | | | | | | |
| Adult BMI Assessment | | | | | | |
| Adults' Access to Preventive/Ambulatory Health Services | | | | | | |
| Annual Monitoring for Patients on Persistent Meds | | | | | | |
| Breast Cancer Screening | | | | | | |
| - BCS - 50-69 | 58% | 63% | 65% | 68% | 72% | 85% |
| Care for Older Adults | | | | | | |
| Cholesterol Management | | | | | | |
| - LDL C Screening | 44% | 60% | 75% | 81% | 79% | 91% |
| Colorectal Cancer Screening | | | | | | |
| - 51-75 yrs Old | 44% | 46% | 50% | 54% | 62% | 77% |
| Comprehensive Diabetes Care | | | | | | |
| - LDL C Screening | 33% | 52% | 69% | 77% | 82% | 90% |
| - HbA1c > 9% | 30% | 46% | 60% | 67% | 71% | 88% |
| - Eye Exam | 3% | 14% | 23% | 28% | 38% | 73% |
| - LDL- C < 100 | 21% | 33% | 43% | 50% | 53% | 64% |

Star and Pay for Performance Measures
Monthly Trend Report
For Measurement Year 2012

FIG. 10

☐ Heritage Provider Network

Your Action Required Now?

Member Information:

Last Name
First Name
Date of Birth
Sex
Member ID
Date

Please discuss the following quality and preventive care services with your physician today.

Recommended Quality and Preventive Care Service(s):

☐ Function Status Assessment
☐ Glaucoma Eye Exam by an Optometrist
☐ Influenza Vaccination
☐ Medication Review If you have had any of the above services performed elsewhere during the current year, please bring copies of the reports, so that the physician has a complete set of your medical records.

FIG. 11

Provider:

Provider name: [_____]

Last name: [_____] [Search]

Provider ID: [_____]

────── OR Type Provider ──────

LName: [_____]

FName: [_____]

Credential: [_____]

Vendor Name: [_____]

Measures:
- x  Controlling High Blood Pressure
- x  Diabetes Care - Eye Exam
- x  Diabetes Care - HbA1c > 9%
- x  Diabetes Care - LDL-C < 100
- »  Diabetes Care - LDL-C < Screening
- »  Diabetes Care - Nephropathy
- x  Influenza Vaccination

[Back to Member list]

Event Code:

| Code Type | Code | Result | DOS | POS | Pages | Upload File |
|---|---|---|---|---|---|---|
| [▼] | [__] | [__] | [_/_/_] | [___▼] | [_/_] | [___] |

⊕ Add Event Code

Exclusion:

Exclusion Reason: [_____▼]  DOS: [_/_/_]  Pages: [_/_]

⊕ Add Exclusion

[SUBMIT ▲]

⇦ TOP

FIG. 12

METHODS FOR OPTIMIZING MANAGED HEALTHCARE ADMINISTRATION AND ACHIEVING OBJECTIVE QUALITY STANDARDS

CROSS-REFERENCE TO RELATED APPLICATIONS

The present application is a continuation of U.S. patent application Ser. No. 15/239,454, filed Aug. 17, 2016 and entitled MULTICOMPUTER DATA TRANSFERRING AND PROCESSING SYSTEM, which is a divisional application of U.S. patent application Ser. No. 13/715,852, filed Dec. 14, 2012 and entitled METHODS FOR OPTIMIZING MANAGED HEALTHCARE ADMINISTRATION AND ACHIEVING OBJECTIVE QUALITY STANDARDS, which is a continuation of U.S. patent application Ser. No. 13/712,776, filed Dec. 12, 2012 and entitled METHODS FOR OPTIMIZING MANAGED HEALTHCARE ADMINISTRATION AND ACHIEVING OBJECTIVE QUALITY STANDARDS, the disclosures of all of which are herein incorporated by reference in their entireties.

STATEMENT RE: FEDERALLY SPONSORED RESEARCH/DEVELOPMENT

Not Applicable

BACKGROUND

In a managed care setting, whether it is for commercial or senior products, health insurance is offered individually, through an employer or through Medicare. In all cases, the patient's coverage often changes. Whether it is a change in benefits or moving out of the service area, providers often move in and out of a patient's ecosystem, which then causes disjointed and incomplete health information and assessment of the quality of care rendered. Along those lines, in our current state of healthcare, there is not enough incentive (funding) to measure every health quality measure to ensure optimal healthcare is administered to eligible recipients. There are variations in the collection and reporting of data as well as the categories that are measured between programs. For example, pay for performance programs tend to allow greater flexibility in the ability to capture supplemental data than some of the other programs but are far limited in the number of quality outcomes measured, especially for the high utilizing senior population.

With these varying programs, as well as many health plans introducing their own quality initiatives, it is almost impossible for providers to keep track of the appropriate health maintenance programs for their patient population and much less insure that quality care is being administered. As a consequence, duplication and errors are more commonplace, causing the quality of care to be negatively impacted.

Moreover, managed care is typically restricted to a specific service area and typically incorporates a referral and utilization management process which thus further limits a continuum of care to be administered. It has likewise not been enough to avoid hospital admissions and bend the cost curve. In such scenario, Pareto's Law applies: 20% of the population accounts for 80% of the costs. In order to truly impact the cost curve, care coordination must take front and center, with an immediate focus on the high risk members.

Even though there are many tools in the marketplace, none understand the problem and provide the means to a solution. The perfect tool needs to interface with a range of healthcare data coming from different payors, Electronic Medical Records (EMR) providers, payment systems and so on so as to accomplish two objectives: 1) accurately diagnosing and tracking each specific patient's medical condition and timely updating such information so as to provide a continuously accurate picture of a patient's health; and 2) ensuring that each specific patient eligible to receive healthcare benefits in a given program are administered such that the quality of care adheres to an objective, high-quality standard so that in all cases each patient receives quality care that is commensurate with the accurately diagnosed condition. Unfortunately, no such systems currently exist.

BRIEF SUMMARY

The present invention specifically addresses and alleviates the above-identified deficiencies in the art. Specifically, in a first component of the present invention, there is provided a comprehensive, readily-accessible assessment of each specific patient's health profile based on aggregated member data from multiple data sources. The comprehensive patient data is compiled from many different sources, namely, electronic health records and electronic medical records (EHR/EMR), insurance claims/encounter data, clinical lab results, filled medications, referrals, admissions, primary care medical records immunization registries, specialist and hospitals reports, and information reported by Centers for Medicare & Medicaid Services (CMS), including both electronic and paper records. Such data is aggregated and stored on a storage medium at a central database and is presented to the providers at the point of service to their members.

Based on the comprehensive data, patient information is gathered and presented to healthcare providers to thus assist providers to make better clinical decisions based on available data. Such data aggregation helps providers understand the member's medical condition better, and assists by ensuring all appropriate medical conditions are treated. To that end, such data is deployed to selectively administer healthcare to specific patients in a patient population (i.e., members or enrollees in a given healthcare plan) in order to assist the providers to provide the highest level of healthcare possible, while reducing their administrative burden by categorizing each of their patients into the appropriate quality programs.

To that end, the present invention uses patients' aggregated healthcare information to generate a population eligible for each of the quality measures of a specific health quality program. In this regard, and as is well-known in the art, numerous objective healthcare administration quality standards have been set that will serve as the objective criteria against which the healthcare administration methods of the present invention are applied to the specific patients in the eligible patient population as warranted based upon the aggregated healthcare and comprehensive patient data. Whether the health quality program is derived by the Centers for Medicare & Medicaid Services (CMS) such as the Five-Star Quality Rating System, National Committee for Quality Assurance (NCQA) such as the Healthcare Effectiveness Data and Information Set (HEDIS) Quality Measures, or Integrated Health Association's (IHA) Healthcare Pay for Performance (P4P) program, the present invention assists in the effective management of such programs to identify quality gaps and triggers with its built-in workflow processes. Specifically, once the eligible population (denominator) has been established, it calculates the set of patients that have fulfilled requirements for the measures (numerator) as well as the ones that have not met the criteria, also known as the non-compliant patients (numerator non-compliant or patients with "quality gaps").

In response, the present invention summarizes the information in usable categories by quality measurement programs, health plans, and providers. It is dynamic enough that a user can create summary reports based on one, two, or all of the categories to ultimately present the information necessary to affect improvement in quality measurement scores as determined by an objective health quality program.

In addition, the present invention provides a decisions support system with comprehensive patient information. Likewise, the systems and methods are web-based, and users can access the patients' information from anywhere the Internet is accessible through a secured login protocol. It can be integrated with any EHR/EMR application to provide a complete history and overview of the patient condition to thus enable healthcare providers to appropriately address any healthcare need that may arise.

BRIEF DESCRIPTION OF THE DRAWINGS

These and other features and advantages of the various embodiments disclosed herein will be better understood with respect to the following description and drawings, in which like numbers refer to like parts throughout, and in which:

FIG. 3 is an exemplary screenshot providing risk adjusted factor comparative analysis between health plans per each respective plan's providers and current year expenses versus previous year expenses.

FIG. 4 is an exemplary screenshot identifying and summarizing comprehensive patient data, as well as objective health quality measures, as measured against an objective, specific health quality program, that are outstanding for an individual patient.

FIG. 5 is an exemplary screenshot displaying compiled information detailing claims, hospital admissions, lab results and medication refills, as well as the specific healthcare provider, designated specialty, diagnosis for which treatment was provided to a patient and the date such services were rendered for a given patient within the eligible patient population.

FIG. 6 is an exemplary screenshot whereby diagnostic information for a specific patient, as represented by a diagnostic code, may be added and/or modified based on a review of available data and scanned medical records.

FIG. 7 is an exemplary screenshot depicting how the methods of the present invention are operative to compile and generate data indicative of the prevalence of one or more diseases/chronic health conditions in a given patient population, as well as the trend in prevalence and costs associated with treatment for a given condition.

FIG. 9 is an exemplary screenshot summarizing specific objective quality measures and how a given plan has achieved specific quality outcomes, as represented in a star-scale format.

FIG. 10 is an exemplary screenshot of a monthly trend report tracking historical compliance scores for each objective quality measure.

FIG. 11 is an exemplary "Boarding Pass" that provides a specific patient with a list of healthcare objectives to be met so as to comply with a given quality control measure.

FIG. 12 is an exemplary screenshot operative to enable information specific to a particular patient regarding specific quality measures that have been met or not met, and providing for supplemental data or exclusions that may apply to that patient for a given quality measure.

DETAILED DESCRIPTION

The detailed description set forth below is intended as a description of the presently preferred embodiment of the invention, and is not intended to represent the only form in which the present invention may be implemented or performed. The description sets forth the functions and sequences of steps for practicing the invention. It is to be understood, however, that the same or equivalent functions and sequences may be accomplished by different embodiments and that they are also intended to be encompassed within the scope of the invention.

Figure 1:
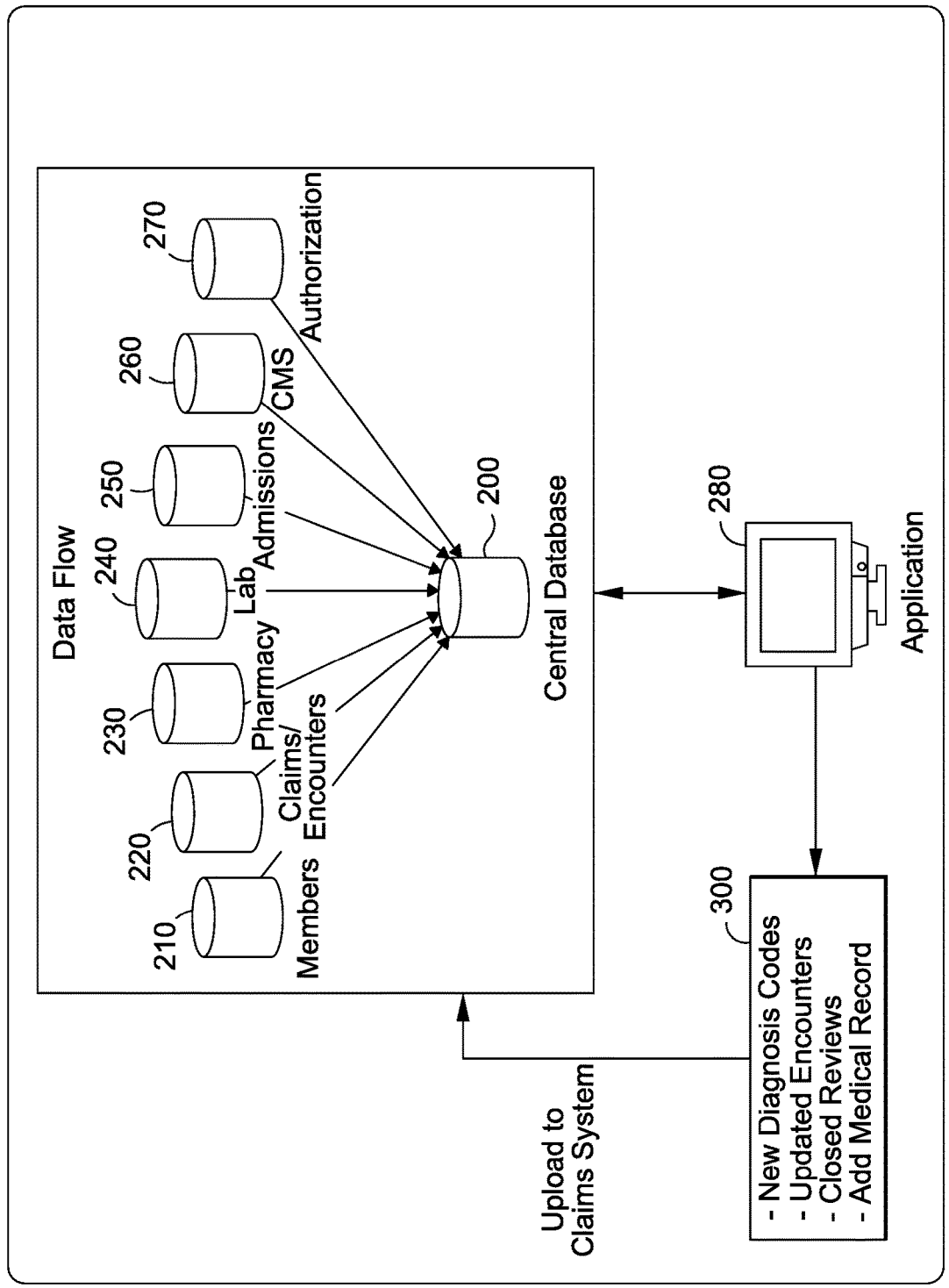
FIG. 1 is a schematic diagram of the computer/server architecture by which healthcare information, compiled from multiple sources, is aggregated for use in patient assessment pursuant to the methods of the present invention.
Figure 1A:
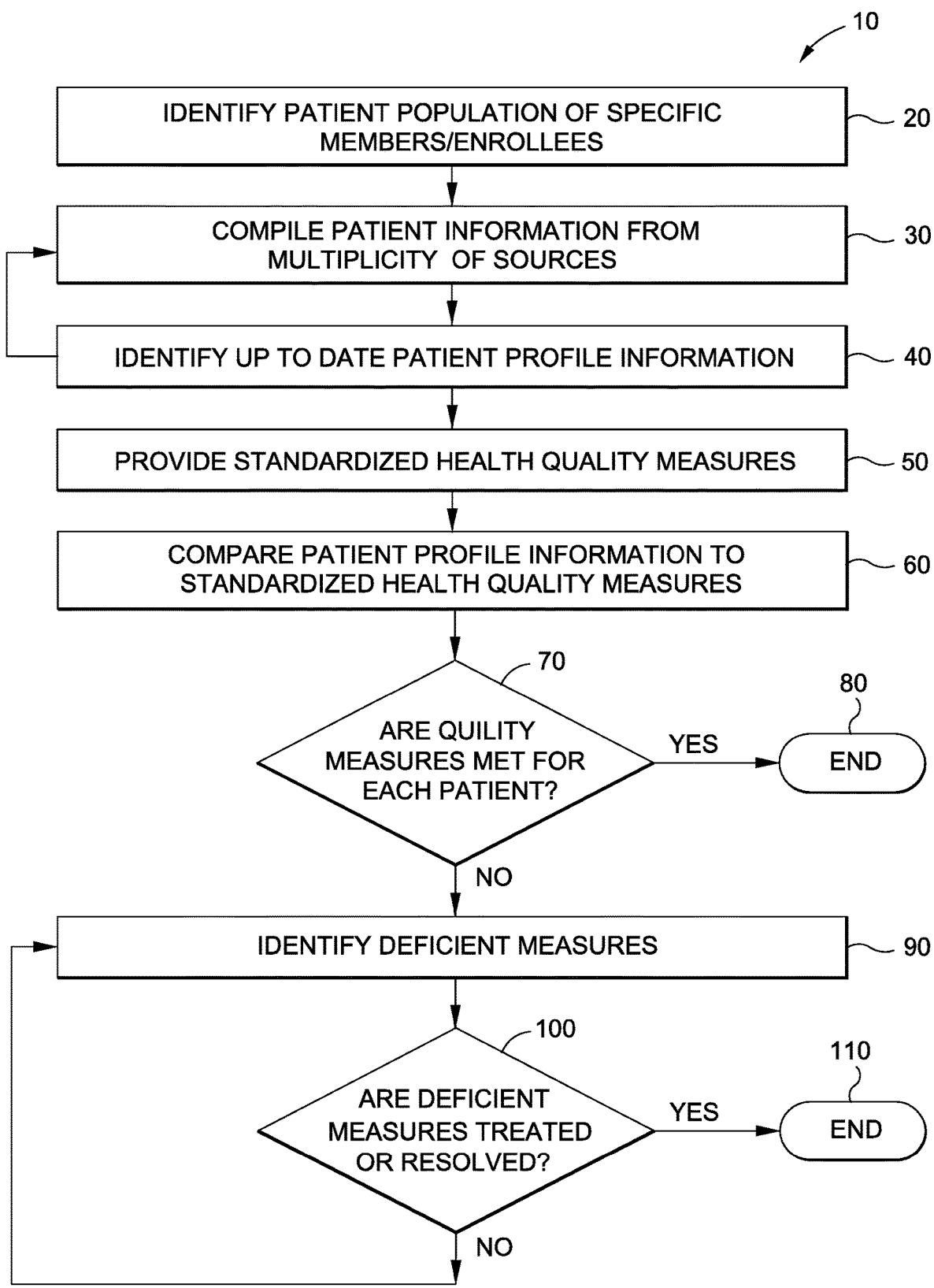
FIG. 1A is flow chart depicting the general steps for performing the methods of the present invention.

Referring now to the drawings, and initially to FIG. 1A, there is shown, generally, a method 10 depicting the steps necessary to: 1) identify a specific patient population of members/enrollees that are eligible to receive healthcare and compiling and tracking all related healthcare information with each respective patient within such population; and 2) administer healthcare to each specific individual member/enrollee within the patient population according to a standardized measure of health quality whereby the care and management of a specific disease, healthcare need and the like will be administered so that healthcare is provided that complies with the standardized health quality measure.

Initially, the process 10 begins with step 20 of identifying a patient population of specific members/enrollees eligible to receive healthcare pursuant to the methods for the present invention. Such step 20 may be accomplished via a variety of conventional methods known in the art whereby eligible patients are enrolled within a healthcare plan. Such step 20, may be accomplished, for example, via the use of application forms, medical screening and the like, coupled with one or more eligible requirements, such as base line health status, age, income and the like.

Once such patient population is identified in step 20, a comprehensive compilation and aggregation of medical information concerning each patient within the patient population is derived from a multiplicity of sources. In this regard, step 30 will involve aggregating patient data from a plurality of databases shown in FIG. 1, that are ultimately compiled and stored in computer readable form on a central database. Specifically, as shown in FIG. 1, the central database 200 will be linked via a telecommunications link to databases associated with membership/enrollee information at 210, databases of the patient's previous insurance claims and encounters 220, pharmacy information 230, including the various medications that have been previously prescribed to the patient, dosage and other relevant information, laboratory results 240, hospital admissions 250, all pertinent data associated with treatment/healthcare services rendered by Centers for Medicare Services (CMS) 260 and any and all information separately stored and accessible concerning prior authorization concerning healthcare services previously rendered to the patient.

As will be appreciated by those skilled in the art, the central database 200 will thus serve as a comprehensive, readily accessible aggregation of patient data that serves as an up-to-date profile of a patient's health status and prior medical history. Such information may be accessed by a remote computer 280 that may be linked to the central database via a web-based application to thus enable the user at 280 to access information on the central database 200 anywhere via the Internet. Along those lines, it is contemplated that access to the central database 200 via remote computer 280 will thus enable healthcare providers to review such information readily, as well as update patient information at step 40 of FIG. 1A, whereby new diagnoses codes, updated encounters, and other information depicted as 300 in FIG. 1, can be entered as part of the patient information stored on the database 200. Ultimately, a patient profile is created and stored on the central database 200 for each patient within the patient population. Each patient profile can thus be readily accessed and provides an assessment of the patient's current health status.

Once the patient population has been defined and the health records of each individual created and updated in the aforementioned manner, a standard of care, preferably an objective standard of care, is provided in step 50 to serve as a basis by which healthcare is administered to the patient population. With respect to the standardized criteria, it is contemplated that any of a variety of known, well-recognized objective criteria of standardized health quality measures may be readily referenced and utilized in the practice of the present invention. Exemplary of such health quality standards include any of those known in the art such as those derived by the Centers for Medicare and Medicaid Services (CMS) such as the five-star quality rating system; National Committee for Quality Assurance (NCQA) standards including the Health Care Effectiveness Data and Information Set (HEDIS) quality measures; or Integrated Health Association's (IHA) Health Care Pay for Performance (P4) Program.

In use, and as depicted in FIG. 1A, the methods of the present invention are operative to continuously monitor, update and compare each of the patient member/enrollee profile information to the standardized health quality measures chosen to be implemented as part of such methods, with each patient continuously being assessed as to whether or not they are being treated in accordance with such standardized healthcare measures per step 60. To that end, such administration of healthcare may take the form of the methods of Applicant's co-pending U.S. patent application Ser. No. 13/712,758, filed Dec. 12, 2012, entitled METHODS FOR ADMINISTERING PREVENTATIVE HEALTHCARE TO A PATIENT POPULATION, the teachings of which are expressly incorporated herein by reference. A decision is then made at step 70 as to whether or not each patient has been adequately treated to meet the standardized quality of care set forth in step 50.

To the extent treatment has been adequately rendered consistent with the standardized criteria, the method ends at step 80. Alternatively, to the extent quality measures have not been met, a further step 90 is performed whereby the specific procedures and/or healthcare necessary to meet the standardized health quality measure at step 50 are identified. Along those lines, such measures may take any of a variety of recognized medical conditions and diseases as compared with the recognized treatment and measures to be implemented to address the specific condition, as set forth in the standardized criteria of step 50.

Thereafter, an assessment is made as to whether or not the deficient measures have been adequately addressed or resolved at step 100, in which case if so the process ends 110. To the extent such deficiencies have not been addressed consistent with the objective criteria, such deficiencies are again identified by repeating step 90 and again evaluating at step 100 as to whether or not the objective criteria have been met until such time as adequate care has been rendered to a desired percentage of the patient population. Along these lines, it is contemplated that providing at least 80% of the eligible patient population with care consistent with the standardized health quality standards of step 50 will be a minimum benchmark. Attaining percentages of 85%, 90% and 95% of eligible patients are optimal targets.

The present invention, through its web-based system of compiling, tracking and updating critical patient data from multiple sources, and comparing the specific needs of each patient with criteria to be met pursuant to the standardized health quality measures, an exceptionally effective and efficient healthcare delivery system is thus defined that not only optimizes healthcare delivery but eliminates waste, prevents outdated patient data from influencing critical healthcare conditions, and ensures that only the most appropriate healthcare is provided which, in turn, substantially conserves healthcare resources and numerous other benefits.

The present invention by which the aforementioned methods are achieved provide other ancillary benefits that are further effective in documenting healthcare administration trends, problem areas, waste and other specific issues related to healthcare administration so as to maximize efficient healthcare administration. As discussed above various databases and medical information from which the present invention draws upon (See FIG. 1) aggregate patient information in real time so as to provide any healthcare provider at any point in time the most up to date information possible regarding the healthcare information of a given individual for use in steps 30 and 40 of FIG. 1A. FIG. 1 further illustrates how the application and web servers are structured for data-transfer and retrieval. In this respect, the plurality of databases are tied to a central database so as to relay information on a constantly updated central database. Such databases preferably include a dedicated database related to each member or enrollee in a given health management plan; the specific claims and encounters each member has had related to physician visits or instances where healthcare has been provided; pharmacy data, including prescription history and the like, a database of all lab work associated with each member, including all relevant clinical findings, a hospital admissions database, a database associated with each and every center for Medicare/Medicaid service has been provided where applicable for each member/enrollee, and lastly a database associated with any and all authorization associated with decisions as to approval or denial of a given procedure, treatment, etc. had been previously determined. Moreover, although not shown, a further database may include any and all electronic medical records/electronic healthcare records (EMR/EHR) that may be associated with a patient that may be further made accessible to provide as accurate and thorough information as possible given the health condition of a given member/enrollee.

In one exemplary embodiment, there is shown in Table 1 below the various types of data that are continuously tracked by the central database, exemplary sources from where the data is derived, and the frequency by which such information is updated (i.e., per step 40 in FIG. 1A). As will be appreciated by those skilled in the art, such medical data as reflected in Table 1 can and will be fluid in nature and constantly changing. Moreover, although the frequency of the rate at which this information is updated may vary, it is believed that Table 1 reflects the most optimal timing (i.e., daily, monthly or as required as indicated respectively) by which such information should be updated.

Along those lines, at present it is contemplated that access to the database supports specific categories of users, namely, the member/enrollee, healthcare provider, management and coder/auditor (i.e., quality control specialists certified to review deficiencies in capturing diagnoses and to capture diagnoses after reviewing the medical records/charts from primary care providers, specialists offices and hospitals).

TABLE 1

| # | Data Type | Exemplary Source of Data | Information Extracted | Frequency |
|---|---|---|---|---|
| 1 | Claims/Encounters | EZ-CAP ® Claims Module | Claims at the member level, aggregate paid amounts, summary of payments at provider and vendor levels | Daily |
| 2 | Membership | EZ- CAP ® Eligibility Module | Member details, summary of eligibility data at vendor and provider levels | Daily |
| 3 | Providers | EZ- CAP ® Provider Module | Provider details | Daily |
| 4 | Utilization | EZ- CAP ® Case Management | Admissions by level of care, length of stay and other case details | Daily |
|   |   | EZ- CAP ® Authentication | All the referral with status |   |
| 5 | Lab Results | Quest/LabCorp | Lab Results | Monthly |
| 6 | Pharmacy Data | Health Plans/PBM | Medication refills with dosage and other details | Monthly |
| 7 | MMR/MOR (Monthly Membership Report/ Medical Overpayment Report) | Health Plans/Primary Benefit Managers (PBM | Member demographics, RAF score and accepted HCC by CMS | Monthly |
| 8 | System/Support | Manual | Diagnosis Hierarchical Condition Categories (HCC) mapping, disease group mapping etc. | As and when required |

With respect to the hardware necessary to implement the foregoing transfer of data between the central database and the various databases connected therewith, such may be accomplished by a variety of computer systems and servers well-known in the art. Presently, it is believed that Microsoft SQL 2005/2008 servers are exemplary of such servers through which the methods of the present invention may be accomplished. Also, it will be readily understood by those skilled in the art that the exemplary sources of data set forth in Table 1 will typically represent well-known and extensively utilized healthcare industry software and databases practiced in the art. For example, the information derived from claims/encounters, membership, providers and utilization can be derived from any of a variety of health plan administration software, including the EZ-CAP® software produced by MZI HealthCare, LLC of Valencia, Calif. that is operative to manage health benefit administration, automation of claims and other healthcare transactions, and oversee financial and medical management. Similarly, lab results can be readily accessed through well-known diagnostic testing providers such as LabCorp Laboratory Corporation of America and Quest Diagnostics. Other sources of data that can be accessed for providing comprehensive patient health information will further be readily appreciated by those skilled in the art.

Given the foregoing architecture and the various databases to which the central database is coupled, it will be understood that a hierarchy of access will be implemented to thus maintain the security and integrity of the various healthcare information stored and accessible in such database, as well as to restrict access to only those having a need to such information.

Provider login is designed to deliver the potential condition reviews and reports at the point of service with the member. Provider can review a one-page member summary information for the member assigned to them which includes member demographic, reviews for potential condition, diagnosis and procedures captured in the claims and encounter data, lab results and pharmacy data along with risk scores and current hierarchical condition categories (HCCs) for the member provider has the ability to "drill down" and selectively target and isolate the information to find more details as well as the ability to view scanned copies of the medical records from primary care and/or specialist offices and hospitals.

Management login is designed to present the reports which helps management team to identify members with certain conditions or comorbidities, and to identify opportunities to improve the risk score. Management users are able to see updated reports such as the comparative risk scores by health plan and by provider, list of members with outstanding reviews by provider and by review category and many more which assists the management team to focus on the specific area where they can exert resources the most effective and efficient way.

Coder login is designed for certified coders and supervisors to review the deficiencies in capturing diagnoses and to capture diagnoses after reviewing the medical records/charts from primary care providers, specialist offices, and hospitals.

Figure 2:
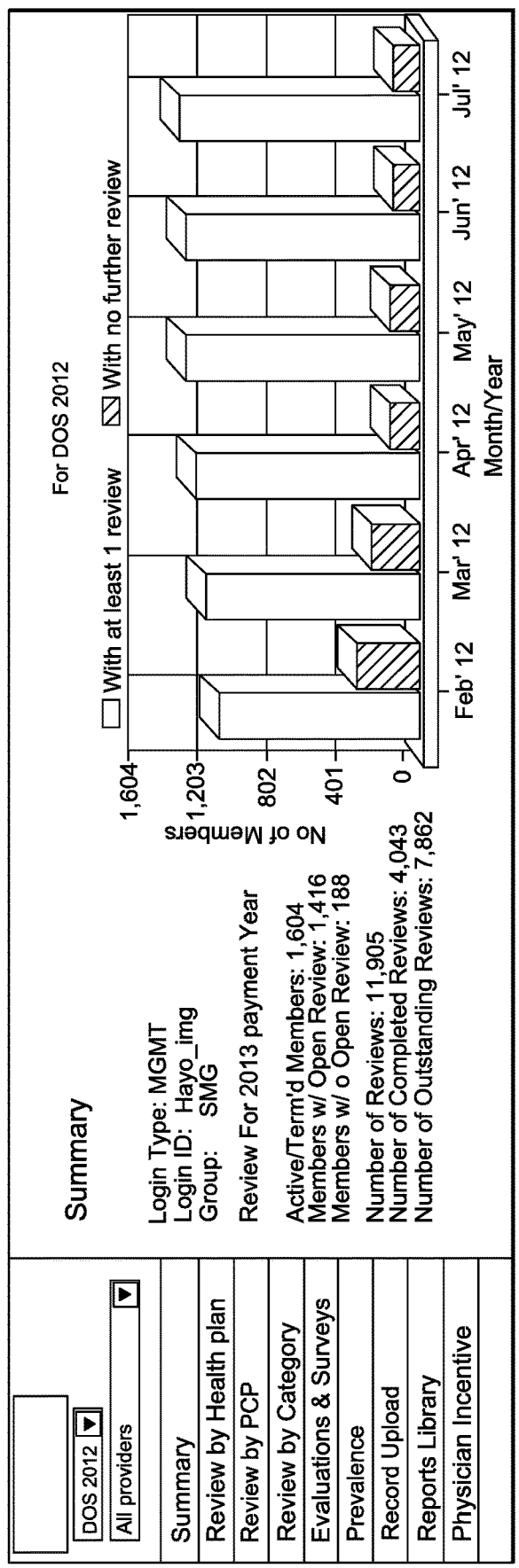
FIG. 2 is an exemplary screenshot summarizing information regarding a specific patient population defined by eligible members/enrollees in a healthcare program with review capabilities as to the healthcare provided to patients within the population.

To begin utilization of the computer systems and methods of the present invention, it is understood that a login process will occur for any of the aforementioned entities after which the applicable user will be directed to a dashboard/homepage. A Dashboard/Home page, as shown in FIG. 2, has summary information on overall membership including active and termed members, number of total reviews, completed reviews and outstanding reviews. The central database allows user to switch between the years to look at the data either for the current year or previous year. Based on the level of access, users will be able to see information for assigned members (Provider login) or all the members (Management login). Management login also has an ability to filter the all the reports for a particular provider to mimic a provider's viewpoint. The left side of the home page as shown in FIG. 2 has menu to navigate the application. Each section has one or more sub-sections or drilldown reports.

Advantageously, the computer/server architecture enables three reports and related drilldown information to be readily derived down to the Primary Care Physician (PCP)/member level. The items, available under this menu are:

Risk Adjusted Factor (RAF): Revenue Current Year (CY) vs. Revenue Previous Year (PY): This report compares two year data by health plan. This report serves multiple purposes, to identify health plans which are attracting sicker membership compared to other health plans which helps management to identify any data deficiency for a particular health plan or opportunity to optimize coding effort.

RAF: Expense Current Year (CY) vs. Expense Previous Year (PY): As shown in FIG. 3, this report compares CY and PY RAF score by health plan for the CY active or termed members which give users an overall RAF score for the same membership between two years.

Open Review/Encounter PMPY: This report gives brief overview of current enrollment, RAF scores (demo and risk) and comparison between CY and PY by health plan.

Similar to the Review by Health Plan section, the present invention further provides the following three reports by PCP and related drilldown information to the member level to thus enable year-to-year revenue and expense comparisons.

RAF: Revenue Current Year (CY) vs. Revenue Previous Year (PY)

RAF: Expense Current Year (CY) vs. Expense Previous Year (PY)

Open Review/Encounter PMPY

Using these reports, management will be able to identify Primary Care Physicians (PCPs) who may have deficiency in coding. Users have the ability to print multiple member summary pages from the list of members assigned to a particular provider. Users can also request medical records and export data to Excel for easier manipulation of data. In addition, users have the ability to review at the member level by selecting member id from reports available under Review by Health Plan and Review by PCP.

As shown in FIG. 4, a member summary page, derived in conjunction with step 30 of method 10 in FIG. 1A, provides comprehensive information about member demographics and health conditions which include:

Member demographic information

Outstanding HEDIS measures

Health status indicator (Primary Care Provider (PCP) visit, ESRD status, Hospice, etc.)

Current year HCCs

Potential health condition

Three year history of HCC/diagnosis

Three year history of procedures

Access to scanned medical records

Medication prescription/refills for the last six months

Lab results for the last twelve months (GFR, CR, Cholesterol, HgbA1C, Microalbumin)

Clinician comments

Figure 5:
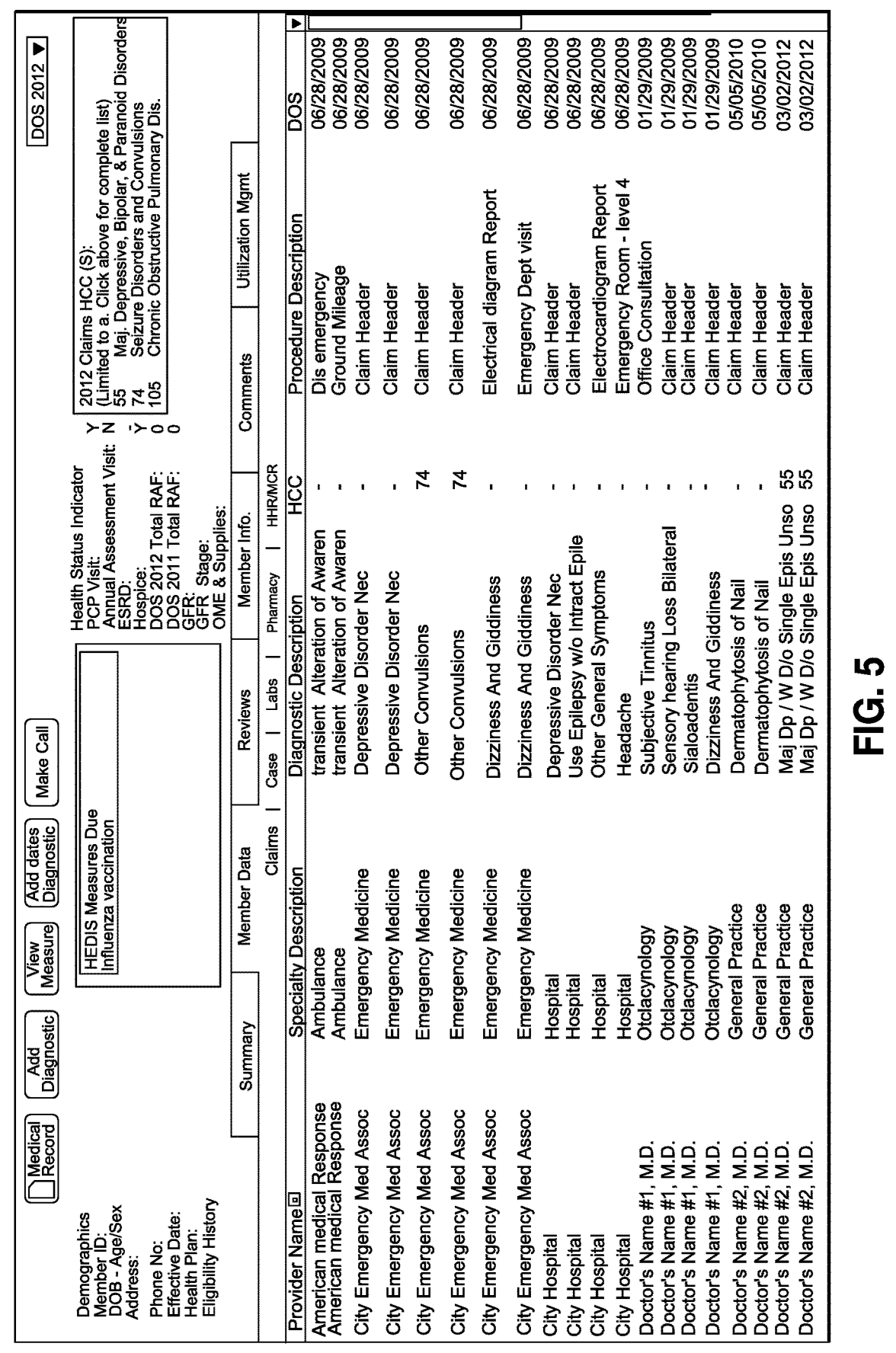

Users can review further detail for claims, admissions, lab results, medication refills in Member Data tab as shown in FIG. 5. The present invention also reports information on how potential health condition is derived under Reviews tab as shown. Member Info tab allows users to request medical records (generate letter) from the PCP. Clinicians and coders have the ability to make comments/notes after reviewing health information and medical records available under the Member Summary Page. User also has ability to see history of all the referrals/authorizations, including referrals status of the selected member.

Figure 6:
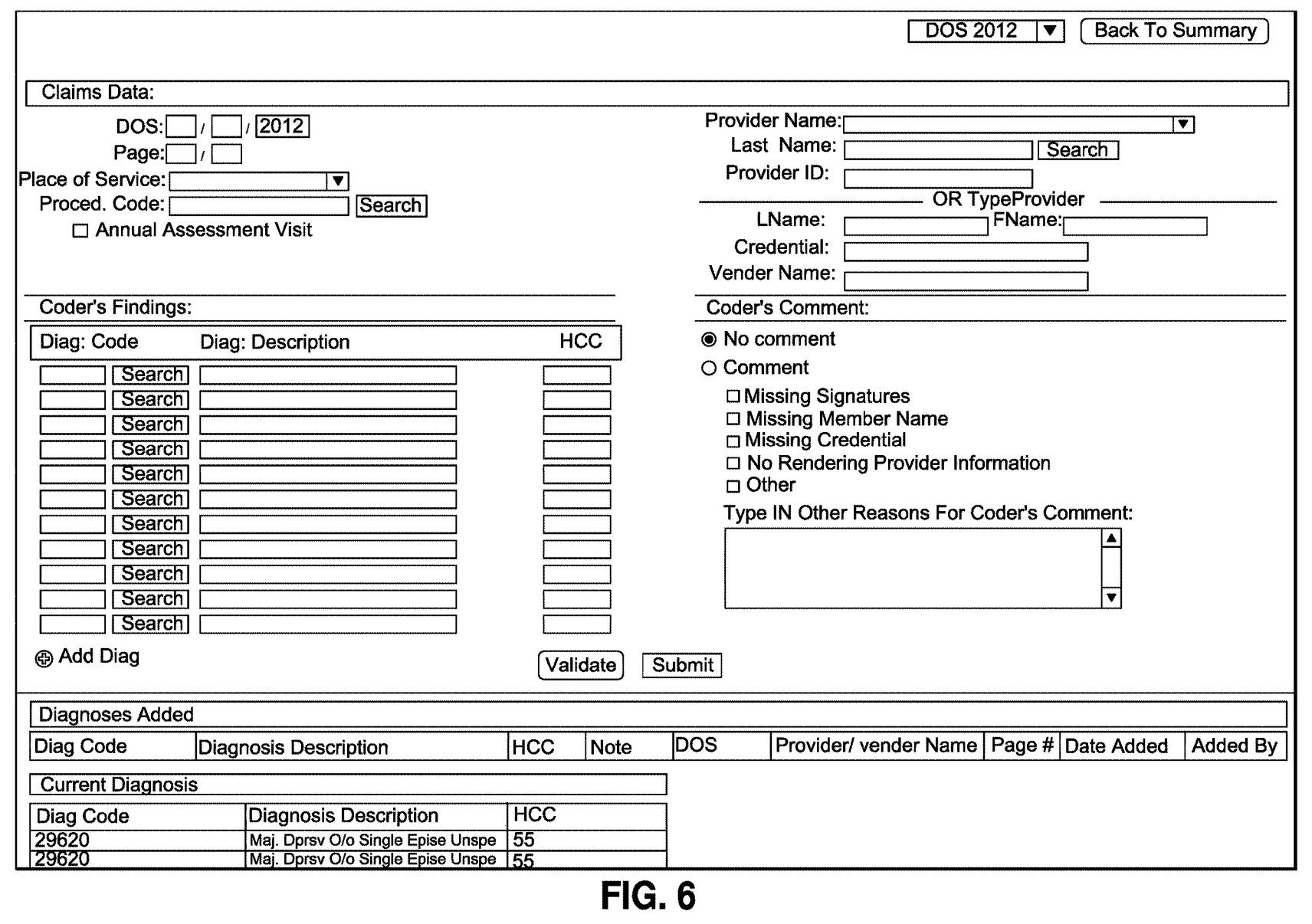

As shown in FIG. 6, Coders (i.e., individuals who review and update patient diagnoses) have the ability to add new encounter/diagnosis based on review of available data and scanned medical records. The present invention has the ability to track the page number from where the coder is coding the diagnoses, which helps the organization provide appropriate back-ups during CMS/Health Plans audit(s). Using multiple edits, the president invention prevents the coder from entering inappropriate diagnoses. If any deficiency exists in the medical charts, the Coder has the ability to add comments while reviewing the medical charts, which in turn gives feedback to providers on improving their deficiencies.

Based on the severity and chronic nature of certain medical conditions that require the most medical attention and utilization of healthcare resources, the systems and methods of the present invention specifically take into account numerous categories that are assigned to specific members/enrollees where applicable, as shown in Table 2 below. Specifically, there are currently eighteen different medical condition review categories that are tracked and generated by the central database using member's claims/ encounters, admissions, lab results, medication refills and MMR/MOR data (again, as part of compiling data in connection with steps 30 and 40 of method 10 of FIG. 1A).

TABLE 2

| 1. Non-Submittable | 2. ESRDCo-Morbidities | 3. High Cost | 4. Pharmacy |
|---|---|---|---|
| 5. Chronic Condition | 6. Correct Coding | 7. Hierarchical | 8. Further Specificity |
| 9. Transplant | 10. Malnutrition | 11. DME | 12. Behavioral Health |
| 13. Cardiovascular | 14. DiabeticCo-Morbidity | 15. Renal | 16. Pulmonary |
| 17. Clinician Review | 18. Prevalence | | |

The present invention additionally allows users to send out surveys to verify the status of working aged members and includes a workflow to make sure members have minimum of one PCP visit during each calendar year so that member's primary care physician can review the member's health condition on an annual basis.

Still further, the present invention is operative to compare a given group's claims/encounter data with CMS published fee for service (FFS) data to identify deficiencies in coding. Also this report helps identify management to review any potential over coding for a particular HCC. As shown in FIG. 7, the database is operative to compare data at the HCC level and allows users to assess healthcare delivery down to the PCP and member level.

As disclosed above, the present invention initially tracks, identifies and aggregates medical information that correctly and thoroughly documents the health history of each member/enrollee in as comprehensive a manner as possible that is further updated on a frequent basis. Because the systems and methods of the present invention so comprehensibly capture and track the medical condition and history of treatment associated with each specific member/enrollee, the present invention is further operative to ensure that the healthcare that is delivered is maintained at whatever level is necessary to meet a given objective criteria of healthcare delivery, as discussed above and more fully below. Advantageously, because the present invention is completely web-based, it allows access to the application from virtually anywhere the user has Internet access and without the need to deploy installation software. Its interface capabilities with Electronic Health Record (HER) systems also provide easy access at the point of care.

To that end, the aforementioned aggregated data is designed to deliver all the capabilities of the application to the healthcare provider for its patient population. This in turn will allow access, either via web-based application access or via EHR interface link, to the provider's patients' quality measurement status preferably at the point of care, as per step 60 of FIG. 1A to thus compare the treatment rendered relative the standard criteria.

Figure 8:
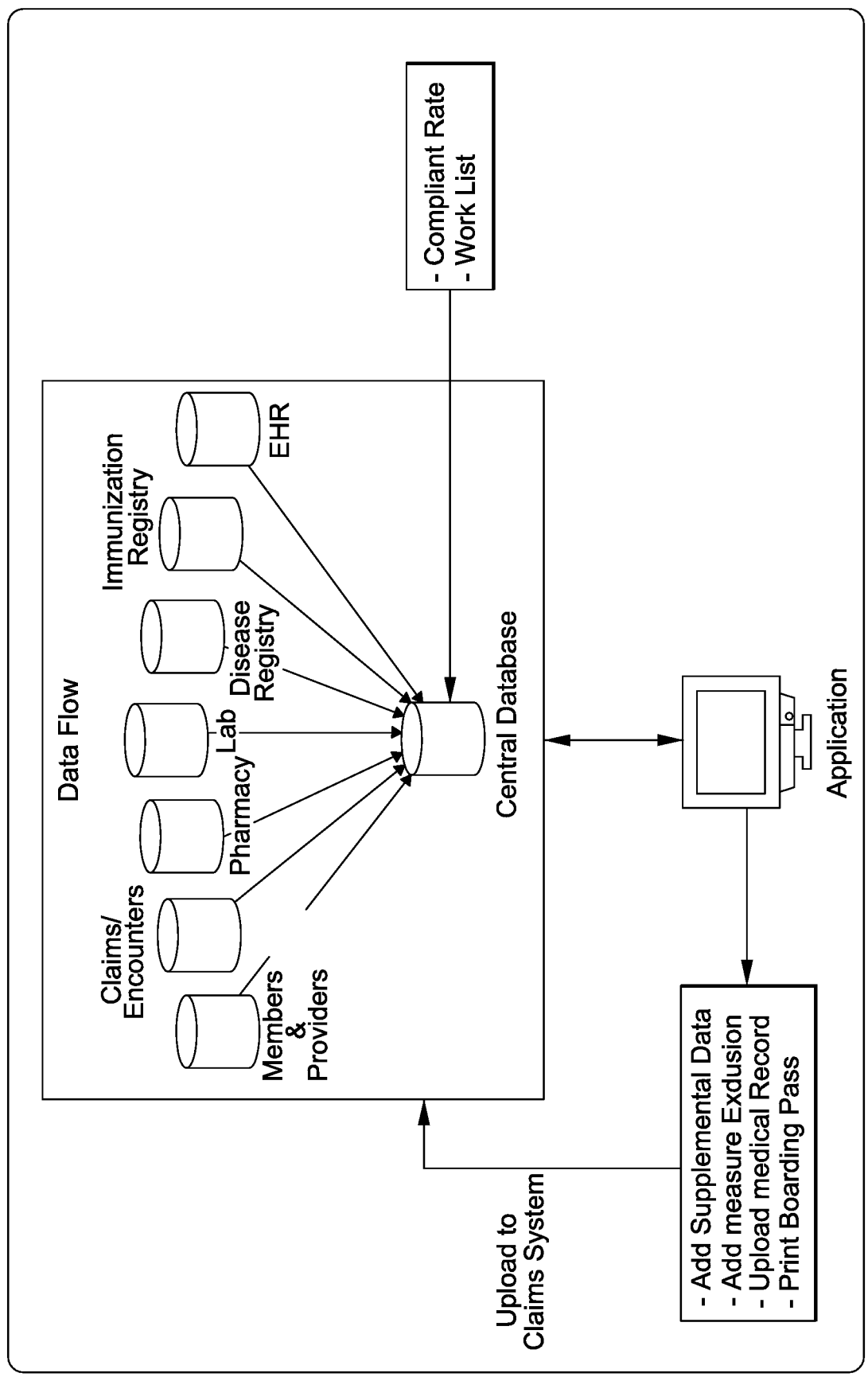
FIG. 8 is a schematic view of the computer/server architecture for use in implementing the administration of healthcare pursuant to an established health quality program.

To determine the optimal healthcare to be provided per steps 70 and 100 of FIG. 1A (i.e., per an objective set of quality measures referred to above), the methods of the present invention likewise deploy a computer/server system to track and implement healthcare measures. Similar to the architecture discussed above with respect to identifying, tracking and aggregating medical data associated with each member/enrollee associated with a given plan, a related architecture is deployed for use in ensuring that the healthcare that is administered to the patient population adheres to an objective set of criteria recognized as meeting each specific patient's healthcare needs. In this regard, there is provided a central database coupled to a plurality of databases whereby the central database aggregates date for use in ensuring that healthcare is administered optimally pursuant to objective criteria, as shown in FIG. 8.

The source data for calculating and categorizing the quality measures are membership, claims and encounter data from the claim processing system, Electronic Health Records (EMR) data, clinical laboratory data, pharmacy data, disease and immunization registry, and other source data. The supplemental data that are captured in central databases can be imported back to the claim processing system via EDI.

As shown in Table 3 below, similar to Table 1, there is provided various types of data, the source from which the data is obtained, the type of data and the frequency by which the data is updated for use in ensuring that healthcare is provided according to quality standards per the methods and systems of the present invention.

As will be understood, such healthcare information may be compiled utilizing existing technology and computer and server hardware. It is likewise contemplated, as discussed above, that a variety of sources are readily known and understood in the art that will provide the sought after data and further, that other sources of data relevant to the patient's receipt of medical treatment may be accessed and integrated to supplement the methods disclosed herein.

TABLE 3

| # | Data Type | Exemplary Source of Data | Information Extracted | Frequency |
|---|---|---|---|---|
| 1 | Claims/Encounters | EZ-CAP ® Claims Module | Claims/Encounters at procedure level | Bi-Weekly |
| 2 | Membership | EZ-CAP ® Eligibility Module | Member details | Bi-Weekly |
| 3 | Providers | EZ-CAP ® Provider Module | Provider details | Bi-Weekly |
| 4 | Utilization | EZ-CAP ® Case Management | Admissions by level of care length of stay | Bi-Weekly |
| 5 | Lab Results | Lab Vendors (Quest/LabCorp) | Clinical Lab Results | Monthly |
| 6 | Pharmacy Data | Health Plans/PBM | Medication refills with dosage and other details | Monthly |
| 7 | Disease Registry | Health Plans/Government | Member Health Records | Monthly |
| 8 | Immunization Registry | Health Plans/Government | Member Health Records | Bi-Weekly |
| 9 | HER/EMR | NextGen | Clinical data | Bi-Weekly |

There are several key functionalities that are derived via such aggregated data that ensures the delivery of high quality healthcare. To identify what measures need to be implemented, the present invention provides a simple, one page outstanding list that can be used by the providers as well as the patients. When dealing with supplemental data capture (i.e., when a measure has been achieved, etc.), not only does it incorporate an intuitive method of capturing the data but also provides medical record upload capability which is essential during reporting audit processes. In cases when removing patients from a quality measure is necessary, the present invention further provides an easy exclusion process which is approved by each quality measurement program.

The Summary by Measures page, as shown in FIG. 9, provides an overall summary for all quality measures, health plans, and in the case for management login, all providers. This is the starting point in determining the overall view of current compliance rates against the benchmarks.

The summary report breaks down the patient population into the line of business, commercial and senior, and further into major categories as defined by the quality measurement programs. It displays the number of patients that are part of the eligible population as well as the ones who are compliant on the quality measures and the ones that are not compliant. The eligible population and the non-compliant patient lists can be generated for each measure by clicking on the respective links for each measure. It also identifies the number of patients that need to be compliant in order to reach the benchmark. For the measures that are part of the CMS Star Ratings program, for example, it also displays the number of stars based on the compliance rate.

As will be appreciated by those skilled in the art, the summary report has very flexible and powerful filtering capabilities. The drop-down lists allow the users to filter by quality measure type, health plan, and providers, or even any combination of all three criteria, via methods well known in the art.

With respect to how each member of the population is actually cared for, the present invention first identifies all of those eligible for treatment and to whom the objective quality standards are measured. This includes each member's demographics as well as the name of their primary care provider. As the members' eligibility changes on a monthly basis, so does the eligible population. As the denominator of a measure changes, the compliance achievement scores are also affected. By displaying the details of the eligible population, the focus of their efforts can be limited to the member population that is currently enrolled in the quality programs.

Since the summary by measures report displays the number of patients that need to qualify for the measure to meet or exceed benchmarks, the Non-Compliant List of member/enrollees, also known as the "care gap" report, provides a list of "To Do" task list to the providers and the management team.

The Non-Compliant List provides a complete list of all patients that have not fulfilled the necessary requirements for a given quality measure. This list, which displays the members' demographics as well as the name of their primary care provider, is very valuable as it is used for many outreach efforts to encourage the patients to perform their preventive care screenings and any disease specific tests such as HgA1C and LDL cholesterol screening as well as breast, cervical and colorectal cancer screening tests.

As an additional feature, there is provided the member search function that can display more than just the list of patients. In addition to the member ID, name, date of birth, and their primary care provider, it displays the number of outstanding measures that the patient has not fulfilled. This provides a quick and easy way to determine whether the patient is in need of any preventive or disease specific quality measures and can alert the nurses, medical assistants, and providers of this fact before a given patient even enters the exam room.

There are also two additional set of information on the member search page which provides a link to the list of outstanding measures via the "Boarding Pass" which can be provided to the patients. In this regard, just as a boarding pass for an airline industry provides pertinent set of information such as where and when to board and where to sit, the present invention is operative to generate a "Boarding Pass." Such Boarding Pass provides the patients the list of what to do, as shown on FIG. 11.

The Boarding Pass provides member demographic information along with all recommended quality and preventive care services that were generated by their quality measurement program. This example shows that this patient requires function status assessment, glaucoma eye exam by an optometrist, influenza vaccination for the upcoming flu season, and a medication review. The boarding pass also provides instructions to the patients that if they have and any of these services performed elsewhere during the current year to bring copies of the reports so that they can be captured in the present invention and to prevent any repeat of unnecessary tests.

This can empower the patient to ensure they are getting all the needed care from their providers and health delivery networks. If the patient has already had the quality measure for which it is displaying as non-compliant, due to possible lag in data refresh or any records that were not captured electronically, the healthcare provider or their staff member can add the supplemental data or exclude a member from a specific measure for any acceptable reason.

In order to track the overall quality measures as provided by a given provider to its patient population, a Monthly Trend report, as shown in FIG. 10, can be generated that keeps track of historical compliance scores for each quality measure exactly in the same format as the Summary by Measures report. This historical data can be used to determine whether certain outreach programs were more successful than others and also determine if there are any cyclical patterns to manage. Indeed, virtually every aspect of healthcare provided to the eligible members of the patient population can readily be assessed for compliance and further, may be adjudged against a benchmark standard.

With respect to the latter, the methods of the present invention are operative to determine the effectiveness of healthcare administration by measuring against all relevant patients eligible to receive healthcare within the patient population have received care according to an objective, standardized metric and measuring trends in that regard. In this respect, the methods of the present invention are operative to identify healthcare administration trends amongst the patients within the patient population, which can include: the number of emergency room encounters, whether ending in a non-admission or an admission; the number of urgent care encounters; the number of hospital admissions per thousand that were not authorized in advance; the number of non-prior-authorized hospital admissions; the number of non-prior-authorized admissions per thousand transferred from other facilities; the length of stay of patients admitted to a hospital, both average and median; the number of office visits, home visits and the like provided by healthcare providers to specific patients within the patient population; and the percent of active members/enrollees within the patient population with updated and complete care plans.

Measurements of each such categories, plus numerous others that will be readily appreciated by those skilled in the art, can be made weekly, monthly, quarterly, semi-annually and annually to identify not only those patients within the patient population that have received healthcare consist with an objective standard of care (CMS five-star quality rating system; NCQA; HEDIS; and/or IHA P4 Program), but how such healthcare is administered over time and how healthcare can be administered so as to decrease high-cost care, such as emergency room visits, hospital admissions, prolonged hospital admissions, and the like.

As a consequence, all eligible members/enrollees within the patient population can be assessed not only in the individual capacity, but as a group as well. Advantageously, the methods of the present invention thus are applicable to not only health plans that treat individuals on a fee for service basis, but also through health maintenance organizations (HMOs) that are operative to allocate a limited number of resources to a patient population. The present invention is further applicable to track and administer care according to such objective standards for as long as the patient remains eligible or enrolled within a specific plan.

To make corrections, deletions and/or additions or may be required in step 100 of FIG. 1A, an Add Supplement Data and Exclusions function, an example depicted in FIG. 12, is provided that allows the users to verify the member demographics before entering any data. Once the correct member record has been selected, the list of outstanding quality measures is displayed with and "x" next to the measure. The measures where they are compliant will also appear but in green color with a check mark next to the name indicating that it has been fulfilled.

After selecting the provider that provided the service, the users are able to enter the list of procedure, diagnosis and other event codes that will trigger a compliant value along with the date of service and the page of the scanned medical record where the data is indicated. The data entered is then verified by the application and if it meets all the criteria, it will convert the outstanding measure with the red "x" to a compliant green check mark.

If the patient has a valid medical reason to be excluded for a quality measure, such as a bilateral mastectomy for the breast cancer screening measure, the qualified exclusion reason can be selected along with the date of service and the supporting medical records. By virtue of such mechanism, the determination is ultimately made as to whether or not a given patient has ultimately been provided the level care commensurate with a given quality measure, and if so, whether the patient's condition has been adequately addressed according to objective standards. Alternatively, such mechanism provides a continuing/persisting condition for a particular patient that warrants continued care pursuant to the objective quality measures provided for a given plan. Still further, such mechanism enables the methods of the present invention, and in particular steps 70 and 90 of FIG. 1A, to be terminated to the extent a given quality measure is no longer needed to address a particular condition, the patient's condition is addressed and/or the patient is no longer eligible or some other event occurs whereby a given measure is no longer applicable for a given patient.

In all circumstances, the present invention thus allows for not only continuous tracking and updating of medical information to always provide the most up-to-date picture of the health profile of every member/enrollee of a patient population, but further that objectively high standards of quality care are administered to each member until such time as such measure is adequately addressed. Per the general steps provided in FIG. 1A, and as discussed more fully above with respect to the various types of data generated through the methods of the present invention and the benefits derived therefrom, optimal healthcare can be delivered that minimizes waste and reliance on potentially inaccurate information in addressing a patient population's healthcare needs.

The above description is given by way of example, and not limitation. Given the above disclosure, one skilled in the art could devise variations that are within the scope and spirit of the invention disclosed herein, including various ways of aggregating medical data concerning a plurality of patients for multiple sources of data that is operative to achieve an accurate diagnosis for each patient within a patient population and thereafter administer healthcare to deliver quality according to a specific health quality program that ensures adequate care commensurate with the specific health conditions of each patient within the patient population is adequately administered. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A system for correcting deficiencies in medical records, the system comprising:
    a central database storing medical records for each of a plurality of patients; and
    a server for providing a remote computer with access to the central database via a web-based application, the web-based application performing operations comprising:
        generating a first screen for displaying a member summary for a specific patient from among the plurality of patients, the member summary including demographic information, potential health conditions, diagnostic history, medical procedure history, and a link to a scanned medical record of the specific patient;
        generating a second screen for displaying diagnostic information for the specific patient, the diagnostic information representing a subset of the diagnostic history displayed on the first screen and including one or more diagnostic codes and a diagnosis description corresponding to each of the one or more diagnostic codes;
        displaying, on the second screen, one or more data entry fields by which an additional diagnostic code may be added to the medical records stored for the specific patient in the central database based on a review of the diagnostic history displayed on the first screen and the scanned medical record of the specific patient;
        applying a plurality of code edits to prevent the addition of inappropriate diagnostic codes into the one or more data entry fields of the second screen using the web-based application; and,
        for each additional diagnostic code added using the web-based application, tracking a page number of the medical records stored for the specific patient in the central database.

2. The system of claim 1, wherein the diagnostic information further includes a hierarchical condition category (HCC) corresponding to each of the one or more diagnostic codes.

3. The system of claim 1, wherein the operations further comprise displaying, on the second screen, a comment input tool by which a user of the web-based application may add comments to the medical records stored for the specific patient in the central database.

4. The system of claim 3, wherein the comment input tool includes a plurality of selectable prewritten comments.

5. The system of claim 4, wherein the comment input tool further includes a text field for adding a comment other than the selectable prewritten comments.

6. A method for correcting deficiencies in medical records, the method comprising:
    storing medical records for each of a plurality of patients in a central database;
    generating, by a web-based application, a first screen for displaying a member summary for a specific patient from among the plurality of patients, the member summary including demographic information, potential health conditions, diagnostic history, medical procedure history, and a link to a scanned medical record of the specific patient;
    generating, by the web-based application, a second screen for displaying diagnostic information for the specific patient, the diagnostic information representing a subset of the diagnostic history displayed on the first screen and including one or more diagnostic codes and a diagnosis description corresponding to each of the one or more diagnostic codes;
    displaying, on the second screen, one or more data entry fields by which an additional diagnostic code may be added to the medical records stored for the specific patient in the central database based on a review of the diagnostic history displayed on the first screen and the scanned medical record of the specific patient;

applying a plurality of code edits to prevent the addition of inappropriate diagnostic codes into the one or more data entry fields of the second screen using the web-based application; and, for each additional diagnostic code added using the web-based application, tracking a page number of the medical records stored for the specific patient in the central database.

7. The method of claim 6, wherein the diagnostic information further includes a hierarchical condition category (HCC) corresponding to each of the one or more diagnostic codes.

8. The method of claim 6, further comprising displaying, on the second screen, a comment input tool by which a user of the web-based application may add comments to the medical records stored for the specific patient in the central database.

9. The method of claim 8, wherein the comment input tool includes a plurality of selectable prewritten comments.

10. The system of claim 9, wherein the comment input tool further includes a text field for adding a comment other than the selectable prewritten comments.

11. A non-transitory computer-readable medium storing instructions executable by a computer to perform operations comprising:

serving a web-based application including a first screen for displaying a member summary for a specific patient from among the plurality of patients, the member summary including demographic information, potential health conditions, diagnostic history, medical procedure history, and a link to a scanned medical record of the specific patient, the web-based application further including a second screen for displaying diagnostic information for the specific patient, the diagnostic information representing a subset of the diagnostic history displayed on the first screen and including one or more diagnostic codes and a diagnosis description corresponding to each of the one or more diagnostic codes;

displaying, on the second screen, one or more data entry fields by which an additional diagnostic code may be added to medical records stored for the specific patient in a central database in communication with the computer based on a review of the diagnostic history displayed on the first screen and the scanned medical record of the specific patient;

applying a plurality of code edits to prevent the addition of inappropriate diagnostic codes into the one or more data entry fields of the second screen using the web-based application; and, for each additional diagnostic code added using the web-based application, tracking a page number of the medical records stored for the specific patient in the central database.

12. The non-transitory computer-readable medium of claim 11, wherein the diagnostic information further includes a hierarchical condition category (HCC) corresponding to each of the one or more diagnostic codes.

13. The non-transitory computer-readable medium of claim 11, wherein the operations further comprise displaying, on the second screen, a comment input tool by which a user of the web-based application may add comments to the medical records stored for the specific patient in the central database.

14. The non-transitory computer-readable medium of claim 13, wherein the comment input tool includes a plurality of selectable prewritten comments.

15. The non-transitory computer-readable medium of claim 14, wherein the comment input tool further includes a text field for adding a comment other than the selectable prewritten comments.

* * * * *